(12) United States Patent
Clarkson et al.

(10) Patent No.: US 6,793,914 B2
(45) Date of Patent: Sep. 21, 2004

(54) ANTI-MICROBIAL COMPOSITIONS

(75) Inventors: Katrin Dagmar Clarkson, Wirral (GB); Andrew Sjaak Landa, Wirral (GB); Stephen Anthony Makin, Wirral (GB); Axel Volker, Buenos Aires (AR)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 82 days.

(21) Appl. No.: 09/764,735

(22) Filed: Jan. 17, 2001

(65) Prior Publication Data

US 2001/0036964 A1 Nov. 1, 2001

(30) Foreign Application Priority Data

Jan. 18, 2000 (GB) ................................ 0001129

(51) Int. Cl.[7] .............................. A61K 7/32; A61K 9/08; A61K 31/197; A61K 31/045; A01N 37/44
(52) U.S. Cl. .............................. 424/65; 424/45; 424/47; 424/401; 424/405; 424/DIG. 6; 514/566; 514/724; 514/739
(58) Field of Search .............................. 424/45, 47, 65, 424/401, 405, DIG. 6, 133.1; 514/566, 724, 739, 499

(56) References Cited

U.S. PATENT DOCUMENTS 4,356,190 A * 10/1982 Kraskin ........................ 424/319

FOREIGN PATENT DOCUMENTS

| EP | 0736804 | 10/1996 |
|----|---------|---------|
| GB | 1420946 | 1/1976 |

OTHER PUBLICATIONS

Journal of Diary Science 68:3037–3046, "*In Vitro Growth Inhibition of Mastitis Causing Baceria by Phenolics and Metal Chelators*", B.P. Chew, L.W. T Joelker and T.S. Tanaka.

Search Report Under Section 17 Application No. GB 00/01129.7 dated May 15, 2000.

* cited by examiner

*Primary Examiner*—John Pak
(74) *Attorney, Agent, or Firm*—Kevin J. Stein

(57) ABSTRACT

An anti-microbial composition employing:

(i) a $C_1$ to $C_4$ monohydric alcohol carrier fluid, present at a level of at least 50% by weight of the total composition (excluding any volatile propellant present);

(ii) an iron (III) chelator having an iron (III) binding constant of $10^{23}$ or greater; and (iii) a solubility promoter such as water:

The transitional metal chelator serves as an active anti-microbial, whilst the carrier fluid-solubility promoter mixture enables the formation of a stable composition. Preferred compositions are homogeneous solutions.

18 Claims, No Drawings

ANTI-MICROBIAL COMPOSITIONS

FIELD OF INVENTION

This invention relates to the field of anti-microbial compositions and to methods of reducing microbial numbers. In particular, this invention is concerned with reducing microbial numbers upon the surface of the human body or upon articles worn in close proximity thereto, thereby reducing malodour. The compositions and methods involved utilise particular iron (III) chelators as anti-microbial agents in compositions also comprising a short chain alcohol and a solubility promoter. When used on the human body, the compositions and methods of the invention are of greatest benefit when used on the most malodorous areas of the human body, for example the underarm areas or feet.

BACKGROUND

Anti-microbial agents may function by a variety of means. When used upon the human body, such agents may significantly reduce microbial numbers either by reducing perspiration or by directly effecting the micro-organisms on the surface of the body as represented herein by skin. It is with this latter class of agents, often called deodorant agents, that this invention is largely concerned.

Most deodorant agents reduce the number of viable micro-organisms on the surface of the skin. It is well known that sweat is usually odourless until it has been degraded by the skin microflora. Typical deodorants include ethanol and triclosan (2',4,4'-trichloro,2-hydroxy-diphenyl ether) which is a well known anti-microbial agent. However, the deodorising effect obtained with such deodorants wears off with the passage of time and the microflora progressively recover their numbers.

There is, therefore, a continuing requirement for effective, long lasting deodorant compositions for the market. The problem to be solved is not simply reducing microbial numbers on the body surface; equally important is maintaining low microbial numbers (particularly low bacterial numbers) on the body surface (particularly in the most malodorous areas, eg. the axillae).

Certain iron (III) chelators have previously been incorporated into deodorant compositions. U.S. Pat. No. 4,356,190 (Personal Products Co.) discloses the use of selected aminopolycarboxylic acid compounds for inhibiting the formation of short chain fatty acids by Corynebacterium on the skin surface. For topical application, alkanolamine salts are stated to be preferred. Especially preferred salts are stated to be di- and trialkanolamine salts such as triethanolamine, diethanolamine, and triisopropanolamine salts. It is also stated that a solvent compatible with the system in which the chelator is incorporated may be employed; however, products comprising mixed solvent systems are not disclosed.

WO 97/02010 (Procter and Gamble Co.) discloses the use of chelators selected from the succinic acid, glutaric acid, and phosphonic acid classes as bactericidal compounds.

WO 97/44006 (Ciba Speciality Chemicals Holding, Inc.) claims the use of particular nitrogen-containing complexing agents for the anti-microbial treatment of the skin and of textile fibre materials. Complexing agents mentioned include those formed from neutralising N,N-ethylenediaminedisuccinic acid (EDDS) with ethanolamine or laurylamine. Deodorant compositions comprising EDDS, ethanol, and water are also disclosed. EDDS has an iron (III) binding constant of $10^{22}$ ("Critical Stability Constants, Volume 1: Amino Acids", p92, Martell and Smith, Plenum Press, 1974.)

WO 97/01360 (Concat Ltd.) claims a method of inhibiting bacterial growth using particular substituted polyaza compounds that show affinity for first transition series elements. It is stated that compatible salts may be formed by neutralisation with inorganic or organic bases, including primary, secondary and tertiary amines, notably ethanolamine, diethanolamine, morpholine, glucamine, N,N-dimethylglucamine, and N-methylglucamine Other patents indicate that iron (III) chelators can improve the efficacy of particular known anti-microbials. WO 89/12399 (Public Health Research Institute of the City of New York) discloses improved performance of lanthionine-containing bacteriocins in compositions also comprising a iron (III) chelator. WO 97/09974 (Laboratoire Medix) discloses compositions comprising chlorhexidine and a chelator. EP 0019670 B1 (Glyco Chemicals, Inc.) discloses anti-microbial compositions comprising a condensation product of 5,5-dimethyl hydantoin and formaldehyde in combination with a water-soluble chelating agent selected from ethylenediaminetetraacetic acid (EDTA), Inc.) discloses the potentiation of anti-microbial nitroalkanes by aminocarboxylic-type chelating agents. U.S. Pat. No. 5,688,516 (University of Texas System et al) discloses compositions comprising non-glycopeptide anti-microbials (other than vancomycin) in combination with a selection of components, including a chelating agent. WO 99/10017 (University of Texas System et al) discloses a method for controlling the growth of micro-organisms using a chelating agent and an anti-microbial agent. GB 1,420,946 (Beecham Group Ltd.) discloses that the activity of selected phenolic anti-microbials can be vastly increased by certain chelating agents, in particular the disodium salt of EDTA.

SUMMARY OF THE INVENTION

This invention is concerned with the formulation of stable, prolonged activity, anti-microbial compositions. The compositions of the invention comprise an alcohol carrier fluid, an iron (III) chelator having an iron (III) binding constant $10^{23}$ or greater, and a solubility promoter selected from a specific group of materials. The particular iron (III) chelators of the invention lead to prolonged anti-microbial activity upon application. The alcohol carrier fluid and solubility promoter enable the chelator to be formulated into a stable, preferably homogeneous, anti-microbial composition.

The prolonged anti-microbial activity often manifests itself as a long-lasting deodorancy benefit, for example lasting a day. Furthermore, in compositions comprising fragrance material, the anti-microbial activity may manifest itself as enhanced fragrance intensity. The stability of the compositions of the invention is a result of good compatibility between the components—this can also lead to benefits in terms of performance and aesthetics. Preferred compositions of the invention are homogeneous solutions. Such solution compositions have advantages with respect to many of the problems associated with alternative suspension compositions; for example, valve blocking, settling and caking of the suspended solids, and uneven application can all be reduced.

Thus, according to a first aspect of the present invention, there is provided an anti-microbial aerosol composition comprising:

(i) a $C_1$ to $C_4$ monohydric alcohol carrier fluid, present at a level of at least 25% by weight of the total composition (excluding any volatile propellant present);

(ii) an iron (III) chelator having an iron (III) binding constant of $10^{23}$ or greater;

(iii) a solubility promoter selected from the group consisting of:
(a) water;
(b) an organic amine;
(c) a polyhydric alcohol or derivative thereof;
(d) a volatile propellant having fluorine-carbon or oxygen-carbon bonds;
(e) any combination of (a) to (d).

According to a second aspect of the present invention, there is provided a method of controlling microbial numbers, said method comprising the application to a substrate of an anti-microbial aerosol composition as provided in accordance with the first aspect of the invention. An application of this aspect of the invention is the control of microbial numbers upon the surface of the human body or upon articles worn in close proximity thereto.

According to a third aspect of the present invention, there is provided a method of inhibiting the generation of malodour comprising the topical application to the human body or to apparel worn in close proximity thereto of a composition as provided in accordance with first aspect of the invention. This method may also be used to deliver enhanced fragrance intensity from a fragrance-containing composition according to the invention.

According to a fourth aspect of the present invention, there is provided a method for the manufacture of an anti-microbial composition, said method comprising the formation of a solution of an iron (III) chelator having an iron (III) binding constant of $10^{23}$ or greater in a $C_1$ to $C_4$ monohydric alcohol carrier fluid, present at a level of at least 25% by weight of the total composition (excluding any volatile propellant present), and also comprising a solubility promoter selected from the group consisting of:

(a) water;

(b) an organic amine;

(c) a polyhydric alcohol or derivative thereof;

(d) a volatile propellant having fluorine-carbon bonds or oxygen-carbon bonds;

any combination of (a) to (d).

DETAILED DESCRIPTION

The novel anti-microbial compositions of the present invention perform unexpectedly well in terms of anti-microbial efficacy and maintenance of low malodour, particularly when applied to the human body. Without wishing to be bound by theory, it is hypothesised that after reduction of microbial numbers by other co-applied agents and/or by some external treatment like washing, the chelator effectively inhibits the up-take of essential transition metal ion nutrients, in particular iron (III), by the remaining microbes, thereby minimising their re-growth.

The above anti-microbial and deodorancy benefits are particularly significant when the composition is applied to a particularly malodorous area of the human body or to apparel worn in close proximity thereto. Thus, it is particularly advantageous to apply the compositions of the present invention to the underarm areas, the feet, and to socks and shoes.

Benefits for fragrance-containing compositions of the present invention have been observed to include enhanced fragrance intensity, particularly when many hours have passed following application. This benefit is believed to be an aspect of the deodorancy benefit, both benefits deriving from the excellent anti-microbial properties of compositions of the invention.

The stability benefit of the compositions of the invention results from making the iron (III) chelator compatible with the alcoholic carrier fluid in the composition. This is done using particular solubility promoters (vide infra). This aspect of the invention also enables formulation of the preferred homogeneous compositions. It is particularly preferred that aerosol compositions are homogeneous solutions, since valve blockage can be a severe problem in such products.

When compositions according to the invention are applied to surfaces, any volatile propellant present evaporates, leaving the chelator, generally dissolved in the carrier fluid and solubility promoter, upon the surface being treated. This solution aspect can lead to significant benefits, both in terms of performance and aesthetics, for example lack of powdery deposits. Preferred compositions comprise a solution of the chelator in the carrier fluid and solubility promoter. Preferably, such solutions have an absorbance, relative to the carrier fluid, of less than 0.2, especially less than 0.1 (for a 1 cm pathlength at 600 nm) measured using a Pharmacia Biotech Ultrospec 200 Spectrophotometer or similar instrument. Preferred compositions are homogeneous solutions. It is preferred that such composition solutions also meet the absorbance criteria set out above: less than 0.2, especially less than 0.1, measured at 600 nm.

The compositions of the invention may be applied to the surface requiring treatment by any means. Whilst direct application is likely to be the most common method for most product uses, pre-application onto a carrier matrix like paper, fabric, or sponge and application by contacting said carrier matrix with the surface, is also a possibility.

Carrier Fluid

The compositions of the present invention comprise greater than 25%, preferably greater than 50%, and more preferably greater than 65%, of $C_1$ to $C_4$ monohydric alcohol carrier fluid, by weight of the total composition (excluding any volatile propellant present). The exclusion of volatile propellant during the calculation of the above values is equivalent to saying that the levels quoted relate the 'base' composition when the composition concerned comprises a volatile propellant. Within the base composition of aerosol compositions, it is further preferred that the alcohol carrier fluid is present at a level in the base composition of greater than 90% by weight, more preferably greater than 95% by weight.

The compositions of the invention preferably have a weight ratio of $C_1$–$C_4$ monohydric alcohol carrier fluid to water of greater than 65:35, more preferably greater than 90:10. In certain particularly preferred compositions, notably aerosol compositions, the weight ratio of $C_1$–$C_4$ monohydric alcohol carrier fluid to water is between 95:5 and 99:1. In other particularly preferred compositions, notably aerosol compositions, the weight ratio of $C_1$–$C_4$ monohydric alcohol carrier fluid to water is greater than 99:1.

The monohydric alcohol carrier fluid is preferably a $C_2$ or $C_3$ alcohol or mixture thereof. Particularly preferred alcohols are ethanol and isopropanol, with ethanol being most preferred.

Iron (III) Chelators

The chelators of the invention have an iron (III) binding constant of $10^{23}$ or greater. Chelators having lower iron (III) binding constants are, in general, less effective in anti-microbial compositions. Chelators having an iron (III) binding constant of $10^{26}$ or greater are preferred, with chelators having an iron (III) binding constant of $10^{28}$ or greater being particularly preferred.

The 'iron (III) binding constant' is the absolute stability constant for the chelator-iron (III) complex. Such values are independent of pH and consider only the most anionic, fully deprotonated form of the chelator. Measurements can be made potentiometrically, and in a number of other ways. Full details of suitable methods can be found in "Determination and Use of Stability Constants", A. E. Martell and R. J. Motekaitis (VCH, New York, 1989). Tables of such values may be found in numerous sources, for example "Critical Stability Constants", R. M. Smith and A. E. Martell (Plenum Pub. Corp., 1977).

Iron (III) chelators are, in general, acids. They may be used as such in the compositions of the invention, although they are preferably used as their salts or acid salts.

In certain preferred compositions of the invention, notably compositions (particularly aerosol compositions) having a ratio of $C_1$–$C_4$ monohydric alcohol to water of greater than 90:10, it is preferred to have the chelator in the form of a salt, or acid salt, with an organic cation. Protonated or quaternised amines are typical of such cations. More information is given relating to the amines used to form such salts in the part of the specification discussing amine solubility promoters.

Chelators salts or acid salts having a mixture of associated cations, including mixtures of both organic and inorganic cations, may also be employed.

The iron (III) chelators used in the present invention preferably have acid forms with at least two, preferably at least four, and most preferably at least five, ionisable acid groups. The acid groups are preferably carboxylic and/or phosphonic, but may be sulphonic or phosphinic, or any mixture of these groups.

Particularly suitable chelators with acid forms having carboxylic acid groups are polycarboxylate compounds, in particular aminopolycarboxylate compounds. The acid forms of the aminopolycarboxylate compounds include ethylenediaminetetraacetic acid (EDTA) and trans-1,2-diaminocyclohexane-N, N,N',N'-tetraacetic acid (CDTA). More preferred aminopolycarboxylate chelators have the acid forms N,N'-ethylenebis[2-(2-hydroxyphenyl)glycine] (EDDHA), triethylenetetraaminehexaacetic acid (TTHA), and diethylenetriaminepentaacetic acid (DTPA). The chelators preferably have only moderate molecular weight, by which it is meant that the chelators, in their acid forms, have a molecular weight of less than 1000, more preferably 200 to 800, and most preferably 290 to 580, and in their salt form have a molecular weight of less than 2000, more preferably 300 to 1400, and most preferably 500 to 1000.

The chelator is preferably incorporated into the composition at a level of 0.01% to 10%, more preferably at a level of 0.05% to 5%, and most preferably at a level 0.3% to 3% by weight of the composition, excluding any volatile propellant present. Mixtures of chelators may also be used.

Solubility Promoter

A solubility promoter selected from the aforementioned alternatives is an essential component of the invention. The choice of solubility promoter is influenced by the nature of the composition and the other components therein. Guidance as to the selection of the solubility promoter is given below.

Water

Water is a preferred solubility promoter in compositions comprising a chelator that is in the form of a salt or acid salt having an inorganic cation or a organic cation formed from a water-soluble amine. The water serves as a solubility promoter by increasing the polarity of the total solvent system.

In compositions for use in roll-on, squeeze spray, or pump spray dispensers, the water is preferably present at a level of from 5 to 50% and more preferably at a level of from 15 to 40% by weight.

In aerosol compositions, the water is preferably present at less than 25%, preferably less than 10%, by weight of the base composition and is preferably used in combination with an organic amine solubility promoter. In aerosol compositions, it is preferred that the weight ratio of $C_1$–$C_4$ monohydric alcohol carrier fluid to water is greater than 65:35, more preferably greater than 90:10. Certain preferred aerosol compositions comprising water have a weight ratio of $C_1$–$C_4$ monohydric alcohol carrier fluid to water of 95:1 to 99:1 and an organic amine solubility promoter. Other preferred aerosol compositions have a weight ratio of $C_1$–$C_4$ monohydric alcohol carrier fluid to water of greater than 99:1 and particular organic amine and/or other solubility promoter(s) present (vide infra).

Compositions with relatively low levels of water can be of particular value in products applied to the human body. When such compositions contain relatively high levels of water, they can sometimes cause an undesirable wet sensation on application. Relatively low water level compositions can also be of benefit with regard to container choice: such compositions enable metal containers to be used with less risk of corrosion. A further benefit of compositions having relatively low water levels is their compatibility with additional hydrophobic components, for example fragrance components (see "Perfumery: practice and principles", R. R. Calkin and S. Jellinek, [Wiley, 1994, p117]).

Organic Amines

An organic amine is a preferred solubility promoter in compositions comprising a weight ratio of $C_1$–$C_4$ monohydric alcohol carrier fluid to water of greater than 75:25 by weight, particularly in aerosol compositions. The organic amine may serve as a solubility promoter by neutralising or partially neutralising acid groups on the chelator, thereby increasing the chelator's solubility in the $C_1$–$C_4$ monohydric alcohol carrier fluid. Quaternised amines may also be employed for this purpose, these amines being conveniently added as their hydroxide salts. The amine is preferably used at a level sufficient to neutralise at least 40%, more preferably at least 60%, of such acid groups. Thus, the preferred amount of amine to be added is dependent upon the amount of chelator present, the relative molecular weights of the amine and the chelator, and the stoichiometry of the neutralisation reaction. For example, it is preferred that at least 2 molar equivalents of a monobasic amine, or at least 3 molar equivalents of a monobasic amine, are added to a chelator possessing 5 acid groups in order to achieve at least 40%, or at least 60%, neutralisation of the acid groups.

Preferably, when an organic amine is employed, the amount added is that which would lead to an aqueous solution of the chelator salt having a pH of between 6 and 8 (at a molar concentration of chelator salt equal to that present in the composition).

Preferred amines are liquids at 20° C. and atmospheric pressure. This can be of advantage with regard to formulation and processing.

Preferred amines are of relatively low odour. This is of potential benefit during manufacture and during selection and use of compositions comprising amine solubility promoters. Related to this point is the preference for amines having relatively low volatility: a boiling point of 130° C. or greater at atmospheric pressure being preferred.

Typical amine solubility promoters of the invention comprise at least one $C_1$–$C_{10}$ terminal hydrocarbyl group; such a group containing solely carbon and hydrogen atoms. Preferred amines of such type are isopropanolamine, 2-amino-2-ethyl-1,3-propanediol, 2-(N,N-dimethylamino)-2-methyl-1-propanol (DMAMP) and N,N- dimethylaminoethanol. Particularly preferred amines are 2-amino-2-methyl-1-propanol (AMP), diisopropanolamine, 2-aminobutan-1-ol, cyclohexylamine, and mixtures thereof. Such relatively hydrophobic amines are of particular benefit in aerosol compositions having a weight ratio of $C_1$–$C_4$ monohydric alcohol carrier fluid to water of greater than 90:10, in particular between 95:5 and 99:1. The benefit is of particular value in aerosol compositions comprising greater than 40% by weight of volatile propellant and of even greater value in aerosol compositions comprising greater than 50% by weight volatile propellant.

When the ratio of $C_1$–$C_4$ monohydric alcohol carrier fluid to water is greater than 99:1, it is preferred that the amine is free of any N—H bonds and/or is free of any O—H bonds (thereby promoting the chelator's solubility in such a hydrophobic system). Such amines can alternatively be described as tertiary amines and/or non-hydroxylated amines. Particularly preferred amines for such compositions are DMAMP, cyclohexylamine, diisopropylamine, tert-butylamine, N,N-diethylhexylamine, and mixtures thereof. This preference is particularly valuable in aerosol compositions, especially those comprising greater than 40% by weight of volatile propellant and of even more especially those comprising greater than 50% by weight volatile propellant.

Polyhydric Alcohol or Derivative Thereof

Solubility promoters that are polyhydric alcohols or derivatives thereof are particularly useful in compositions having a weight ratio of $C_1$–$C_4$ monohydric alcohol carrier fluid to water of greater than 90:10, particularly in aerosol compositions. The polyhydric alcohol or derivative thereof generally serves as a solubility promoter by increasing the polarity of the total solvent system. The amount of polyhydric alcohol or derivative thereof employed is preferably between 1% and 20% by weight, more preferably between 5% and 15% by weight, of the composition, excluding any volatile propellant present.

This form of solubility promoter is preferably used in combination with an organic amine solubility promoter. Particularly great benefits are found in aerosol compositions, especially those having a weight ratio of $C_1$–$C_4$ monohydric alcohol carrier fluid to water of greater than 95:5, more particularly when said ratio is greater than 99:1. Benefits for polyhydric alcohols or derivatives thereof are also of great worth in aerosol compositions comprising greater than 40% by weight of volatile propellant and of even greater value in aerosol compositions comprising greater than 50% by weight of volatile propellant.

The polyhydric alcohols of the invention are materials having at least two hydroxyl groups on a carbon backbone (optionally interrupted by hetero-atoms). The derivatives are esters, ethers, and carbonates, including partial esters and ethers. Preferred polyhydric alcohols are alkane-diols, such as 1,2-diols of $C_2$ to $C_{12}$ alkanes. Preferred derivatives are esters, such as $C_2$ to $C_{12}$ di-esters of 1,2-diols of $C_2$ to $C_3$ alkanes, and carbonates, such as cyclic carbonates like propylene carbonate.

Preferred polyhydric alcohols and derivatives thereof are of molecular weight 60 to 500. Particularly preferred materials are 1,2-pentanediol, 1,2-hexanediol, 1,2-octanediol, propylene glycol, propylene glycol dicaprate/caprylate, and mixtures thereof.

Volatile Propellant having C—O or C—F Bonds

When these materials are used in aerosol compositions according to the invention, the solubility of the chelator is substantially promoted. Such propellants are generally used in combination with an organic amine solubility promoter and usually in compositions comprising a weight ratio of $C_1$–$C_4$ monohydric alcohol carrier fluid to water of greater than 90:10. The amount used is typically from 15% to 99% and preferably from 35% to 87% by weight of the composition. Mixtures of volatile propellants having carbon-oxygen or carbon-fluorine bonds may also be employed, as may mixtures with volatile propellants not having carbon-oxygen or carbon-fluorine bonds (vide infra).

Preferred volatile propellants of this description are dimethylether, 1,1-difluoroethane, 1-trifluoro-2-fluoroethane, carbon dioxide, and mixtures thereof. Partcularly preferred are dimethylether and 1,1-difluoroethane.

Additional Components

Volatile Propellants

Aerosol compositions are a preferred form of the present invention and preferably comprise from 30 to 99% by weight, and particularly 35 to 87% by weight, of a volatile propellant. Said volatile propellant may include one having C—F or C—O bonds, as previously described as a solubility promoter. In addition to such materials, the volatile propellant may be selected from liquefied nitrogen or liquified hydrocarbon gases that have a boiling point of below 10° C. and especially those with a boiling point below 0° C. The liquefied hydrocarbon gas is preferably a $C_3$ to $C_6$ hydrocarbon, including propane, isopropane, butane, isobutane, pentane and isopentane and mixtures of two or more thereof. Particularly preferred volatile propellants are isobutane, isobutane/isopropane, isobutane/propane and mixtures of isopropane, isobutane and butane.

When the volatile propellant is present at a level greater than 40% by weight of the composition, and particularly when it is greater than 50% by weight of the composition, it is preferred that the solubility promoter is selected from the group comprising:

(a) organic amine free of any N—H bonds and/or O—H bonds;

(b) an organic amine and a polyhydric alcohol or derivative thereof;

(c) an organic amine and a volatile propellant having fluorine-carbon or oxygen-carbon bonds.

The above preference to solubility promoters is particularly valid in compositions having a weight ratio of $C_1$–$C_4$ monohydric alcohol carrier fluid to water of between 95:5 and 99:1, and when said ratio is greater than 99:1. The amounts of solubility promoters desirably present are as previously described herein.

Additional Anti-microbial Agents

An additional component that can sometimes augment the efficacy of a composition of the invention is an additional anti-microbial agent. Most of the classes of agents commonly used in the art can be incorporated into compositions of the invention. Levels of incorporation are preferably from 0.01% to 3%, more preferably from 0.03% to 0.5% by weight of the composition, excluding any volatile propellant present. Preferred additional anti-microbial agents have a minimum inhibitory concentration (MIC) of 1 $mg.ml^{-1}$ or less, particularly 200 $\mu g.ml^{-1}$ or less, and especially 100 $\mu g.ml^{-1}$ or less. The MIC of an anti-microbial agent is the minimum concentration of the agent required to significantly inhibit microbial growth. Inhibition is considered "significant" if an 80% or greater reduction in the growth of an inoculum of a relevant micro-organism is observed, relative to a control medium without an anti-microbial agent, over a period of 16 to 24 hours at 37° C. The "relevant micro-organism" used for testing should be representative of those associated with the substrate to be treated. When the substrate to be treated is human skin, a relevant micro-organism is *Staphylococcus epidermidis*. Details of suitable methods for determining MICs can be found in "Antimicrobial Agents and Susceptibility Testing", C. Thornsberry, (in "Manual of Clinical Microbiology", 5$^{th}$ Edition, Ed. A. Balows et al, American Society for Microbiology, Washington D.C., 1991). A particularly suitable method is the Macrobroth Dilution Method as described in Chapter 110 of above publication (pp. 1101-1111) by D. F. Sahm and J. A. Washington II. MICs of anti-microbials suitable for inclusion in the compositions of the invention are triclosan: 0.01–10 $\mu$g.ml$^{-1}$ (J. Regos et al., Dermatologica (1979), 158: 72–79) and farnesol: ca. 25 $\mu$g.ml$^{-1}$ (K. Sawano, T. Sato, and R. Hattori, Proceedings of the 17$^{th}$ IFSCC International Conference, Yokahama (1992) p.210–232). By contrast ethanol and similar alkanols have MICs of greater than 1 mg.ml$^{-1}$. Preferred anti-microbials are bactericides, in particular organic bactericides, for example quaternary ammonium compounds, like cetyltrimethylammonium salts; chlorhexidine and salts thereof; and diglycerol monocaprate, diglycerol monolaurate, glycerol monolaurate, and similar materials, as described in "Deodorant Ingredients", S. A. Makin and M. R. Lowry, in "Antiperspirants and Deodorants", Ed. K. Laden (1999, Marcel Dekker, New York). More preferred anti-microbials for use in the compositions of the invention are polyhexamethylene biguanide salts (also known as polyaminopropyl biguanide salts), an example being Cosmocil CQ™ available from Zeneca PLC, preferably used at up to 1% and more preferably at 0.03% to 0.3% by weight; 2',4,4'-trichloro,2-hydroxy-diphenyl ether (triclosan), preferably used at up to 1% by weight of the composition and more preferably at 0.05–0.3%; and 3,7,11-trimethyldodeca-2,6,10-trienol (farnesol), preferably used at up to 1% by weight of the composition and more preferably at up to 0.5%.

Inorganic anti-microbial agents may also be used in the compositions of the invention. Such materials often also function as anti-perspirant agents. Examples are often selected from astringent active salts, including, in particular, aluminium, zirconium and mixed aluminium/zirconium salts, including both inorganic salts, salts with organic anions and complexes. Their use should take into account local regulations concerning the incorporation of zirconium compounds into cosmetic or aerosol products. Preferred astringent salts include aluminium, zirconium and aluminium/zirconium halides and halohydrate salts, such as chlorohydrates. When included, preferred levels of incorporation are from 0.5% to 60%, particularly from 5% to 30% or 40% and especially from 5% or 10% to 30% or 35% by weight of the composition. Especially preferred aluminium halohydrate salts, known as activated aluminium chlorohydrates, are described in EP 6,739 (Unilever PLC and NV). Zirconium aluminium chlorohydrate actives are also preferred materials, as are the so-called ZAG (zirconium-aluminium-glycine) complexes, for example those disclosed in U.S. Pat. No. 3,792,068 (Procter and Gamble Co.). Zinc phenol sulphonate may also be used, preferably at up to 3% by weight of the composition.

It should be noted that incorporation of amphoteric or cationic anti-microbial agents makes it particularly important to use the compositions of the present invention comprising an organic amine solubility promoter. This is particularly true of organic anti-microbial agents, of cationic anti-microbial agents, and especially true of organic polycationic anti-microbial agents. In this context, "polycationic" means possessing more than one positive charge, although the importance of the use of chelator salts in accord with the present invention is even greater in the presence of organic polycationic anti-microbial agents that possess more than five positive charges per molecule.

Phenolic Anti-Oxidants

These materials can also augment the efficacy of compositions of the invention. Preferred materials for incorporation into compositions of the invention are butylated hydroxytoluene (BHT) and butylated hydroxyanisole (BHA). Such agents are preferably used at 0.05% to 5%, more preferably 0.075% to 2.5%, and most preferably 0.1% to 1% by weight of the composition, excluding any volatile propellant present.

Sensory Modifiers

Certain sensory modifiers are further desirable components in the compositions of the invention. Emollients, humectants, volatile oils and non-volatile oils are all suitable classes of sensory modifiers. Examples of such materials include cyclomethicone, dimethicone, dimethiconol, isopropyl myristate, isopropyl palmitate, C12–C15 alcohol benzoate, PPG-3 myristyl ether, octyl dodecanol, C7–C14 isoparaffins, di-isopropyl adipate, isosorbide laurate, PPG-14 butyl ether, glycerol, hydrogenated polyisobutene, polydecene, phenyl trimethicone, dioctyl adipate, and hexamethyl disiloxane.

Fragrance, etc.

Fragrance is also a desirable additional component in the compositions of the invention. Suitable materials include conventional perfumes, such as perfume oils and also include so-called deo-perfumes, as described in EP 545,556 and other publications. Levels of incorporation are preferably up to 4% by weight, particularly from 0.1% to 2% by weight, and especially from 0.7% to 1.7% by weight of the composition, excluding any volatile propellant present. A fragrance solubiliser is also a desirable component in many compositions. Such materials are emulsifiers that aid the dissolution/dispersion of a fragrance material in a composition. Preferred levels for incorporation are from 0.05% to 2%, preferably from 0.1% to 0.5%, by weight of the composition, excluding any volatile propellant present. These materials are of particular value when the ratio of water to $C_1$ to $C_4$ monohydric alcohol carrier fluid is greater than 25:75 and especially when it is greater than 35:65. Preferred materials are nonionic surfactants of HLB from 5 to 20 and particularly preferred materials include ehoxylated fatty alcohols, ethoxylated fatty acids, and ethoxylated oils, an example of the latter being PEG-40 hydrogenated castor oil.

Other Additives

Further additional components that may also be included are colourants, preservatives, for example C1–C3 alkyl parabens, and anticlogging agents, at conventional concentrations.

It should be noted that certain components of compositions perform more than one function. Such components are particularly preferred additional ingredients, their use often saving both money and formulation space. Examples of such components include isopropyl myristate.

Methods of Manufacture

The compositions of the invention are generally manufactured by forming of a solution of the iron (III) chelator in the carrier fluid plus solubility promoter. A particularly preferred method comprises the addition of the chelator and an organic amine to water to form an aqueous solution, followed by dilution with the $C_1$ to $C_4$ monohydric alcohol carrier fluid to form an aqueous alcohol solution, optionally followed by pressurisation with a liquified volatile propellant. Further details of specific anti-microbial compositions are given in the Examples.

EXAMPLES (Note that "letter" codes refer to Comparative Examples.)

Example 1

Preparation of an Aerosol Deodorant Composition 0.52 g of DTPA was added as a powder to 65.91 g of 96% (w/w) ethanol. To this mixture was added (dropwise, with stirring) 0.38 g of AMP. The resulting mixture was stirred, with gentle heating (50° C.) for 30 minutes. 0.34 g of isopropyl myristate was added to the resulting solution and mixed in. The resulting mixture was sealed into a conventional aluminium deodorant can, having valve access, and 36.16 g of liquified propellant (CAP 40, ex Calor) was introduced into the can from a propellant 'transfer can', via the valve, using a polyethylene transfer device. Finally, the can was fitted with a suitable actuator to enable effective spray application of the product.

Deodorancy Test 1

An anti-microbial composition according to the current invention (Example 1) and a control composition (Comparative Example A—lacking the chelator and amine solubility promoter, see Table 1 for compositions) were prepared according to the method described. The deodorancy performances of the two compositions were tested according to the following protocol. The results, presented in Table 1, illustrate the deodorancy benefit obtained from using an example prepared according to the invention. This benefit is a direct result of the anti-microbial performance of the composition.

Deodorancy Protocol

The panel employed comprised 50 individuals who had been instructed to use control ethanolic deodorant products during the week prior to the test. At the start of the test, panellists were washed with unfragranced soap and test product (1.20 g) applied to one axilla and control product applied (1.20 g) to the other. (Product application was randomised to take into account any left/right bias). Panellists were instructed not to consume spicy food or alcohol, and not to wash under their own axillae, during the duration of the test. At least three expert assessors determined the intensity of axillary malodour at 5 hours and 24 hours after application, scoring the intensity on a scale of 1–5. After each 24 hour assessment, the panellists were re-washed, and products re-applied, as above. The procedure was repeated 4 times. At the end of the test, the data were analysed using standard statistical techniques.

TABLE 1

DTPA-AMP salt vs. Control

| Component | Example A | Example 1 |
| --- | --- | --- |
| DTPA[1] (as free acid) | 0 | 0.51 |
| AMP[2] | 0 | 0.37 |
| Isopropyl myristate[3] | 0.33 | 0.33 |
| CAP40[4] | 35 | 35 |
| Ethanol (96%) | to 100 | to 100 |
| Mean malodour intensity[5] 5 hour | 2.2 | 1.86 |
| Mean malodour intensity[5] 24 hour | 2.36 | 2.01 |

All components are expressed as weight percent of the total components added.
[1]diethylenetriaminepentaacetic acid.
[2]2-amino-2-methyl-1-propanol, used to form the amine salt of the chelator.
[3]Emollient.
[4]Propellant, proprietary mix of butane, isobutane and propane, ex. Calor.
[5]The malodour differences between the compositions were significant at the 99% level, after both 5 hours and 24

Anti-Microbial Test 1

Example 2, indicated in Table 2, was prepared in a similar manner to example 1 and was subjected to the following in vivo test for anti-microbial activity, together with comparative Example A.

The panel employed comprised 27 males who had been instructed to use control ethanolic deodorant products during the week prior to the test. During the first week of the test, panellists' axillae were washed each morning with unfragranced soap and no deodorant products were applied. During the second week of the test, the wash procedure was followed by the application of test product (1.20 g) to one axilla and control product (1.20 g) to the other. (Product application was randomised to take into account any left/right bias). Panellists were instructed not to consume spicy food or alcohol, and not to wash under their own axillae, during the duration of the test.

During the second week, samples of axillary microflora were extracted from each of the panellists immediately before the morning wash (on one of the weekdays other than the first). The axillary microflora were extracted by washing with a phosphate buffer. The extract was subjected to serial dilution and plating on selective media. This enabled the determination of the number colony forming units (CFU) of Coryneform bacteria, Staphylococci bacteria, and total aerobic bacteria per square cm of axillary skin. At the end of the test, the data were analysed using standard statistical techniques.

TABLE 2

Anti-microbial Results

| Component | Example A | Example 2 |
| --- | --- | --- |
| DTPA (as free acid) | 0 | 0.5 |
| AMP | 0 | 0.38 |
| Isopropyl myristate | 0.33 | 0.33 |
| Butylated hydroxytolunene | 0 | 0.10 |
| CAP40 | 35 | 35 |
| Ethanol (96%) | to 100 | to 100 |
| Results | ($\log_{10}$CFU)cm$^{-2}$ | |
| Staphylococci spp. | 5.63 ± 0.74 | 4.29 ± 0.82 |
| Coryneform spp. | 4.64 ± 1.40 | 3.46 ± 1.52 |
| Total Aerobic bacteria | 5.68 ± 0.78 | 4.36 ± 0.87 |

All components are expressed as weight percent of the total components added.

These results illustrate the anti-microbial benefit of compositions according to the invention. Each of the reductions in bacterial numbers was significant at the 99% level. (The Staphylococci result was significant at the 99.9% level.)

Deodorancy Test 2

The deodorancy protocol described above was also used to test the performance of Examples B and 3 (see Table 3).

These Examples were prepared in a similar manner to Examples A and 1, with the modification that a fragrance material was added to the compositions shortly before introduction into the conventional aluminium deodorant cans. The results indicate that the benefit from compositions of the invention is also found in fragrance-containing compositions.

TABLE 3

Fragranced DTPA-AMP salt vs. Fragranced Control

| Component | | Example B | Example 3 |
|---|---|---|---|
| DTPA (as free acid) | | 0 | 0.5 |
| AMP | | 0 | 0.37 |
| Isopropyl myristate | | 0.33 | 0.33 |
| Water | | 2.53 | 2.49 |
| CAP40 | | 35 | 35 |
| Fragrance | | 1.5 | 1.5 |
| Ethanol | | To 100 | To 100 |
| Mean malodour | 5 hour | 1.34 | 1.13 |
| intensity | 24 hour | 2.07 | 1.71 |

All components are expressed as weight percent of the total components added.

The malodour differences between the compositions were significant at the 99% level, after both 5 hours and 24 hours. (Minimum differences required for significance at the 95% and 99% confidence levels were:

after 5 hours: 0.10 for 95% level; 0.13 for 99% level;

after 24 hours: 0.10 for 95% level; 0.13 for 99% level).

Anti-Microbial Test 2

The chelators indicated in Table 4 were subjected to the following in vitro test for anti-microbial activity against *Staphylococcus Epidermididis*.

An axillary isolate of *S. epidermidis* was grown overnight in 100 ml of tryptone soy broth (TSB, ex Oxoid Ltd.). 10 ml of this culture was taken and subjected to centrifugation. The separated cells were re-suspended in 10 ml of phosphate-buffered saline and the centrifugation procedure repeated. The washed cells were re-suspended in 10 ml of phosphate-buffered saline to give the inoculum.

100 ml of semi-synthetic medium (SSM) [containing $(NH_4)_2SO_4$ (0.066 g), $MgSO_4.7H_2O$ (0.012 g), KCl (0.1 g), $KH_2PO_4$ (0.27 g), $Na_2HPO_4$ (1.43 g), Thiamin (0.1 mg), Biotin (0.05 mg), Peptone P (0.05 g), Glucose (2.0 mmole)] was sterilised by autoclaving at 121° C. for 20 minutes. After sterilisation, the pH was adjusted to 6.7 with HCl to give the control medium. The chelator-containing test media were prepared in a similar manner, the chelator being introduced at a concentration of $5\times10^{-5}$ $mol.dm^{-3}$, before the pH adjustment with HCl.

100 μl of the inoculum was introduced into each of the test media and the control medium. The cultures were incubated at 37° C. (with agitation at 200 rpm) for 16 hours. After this time, the optical density of the cultures were measured at 600 nm to determine the extent of bacterial growth. By comparing the optical density of the culture in the presence of chelating agent to that of the control, the percentage inhibition of growth was established for each of the chelators. (Optical density measurements were made on 1 in 4 dilutions of the cultures with 0.9% (w/v) saline, using 1 cm path length cuvettes, on a Pharmacia Biotech Ultrospec 200 Spectrophotometer.)

TABLE 4

Results of Anti-microbial Activity Test

| Chelator | $Log_{10}K$ | Inhibition of growth (%) |
|---|---|---|
| EDDHA | 35.5 | >70 |
| DTPA | 28.6 | >70 |
| CDTA | 28.05 | >70 |
| TTHA | 26.8 | >70 |
| EDTA | 25.1 | >70 |
| EDDS | 22.0 | 18 |
| EGTA[1] | 20.5 | 21 |
| NTA[2] | 15.9 | 6 |

[1]Ethyleneglycol-O,O'-bis-(2-aminoethyl)-N,N,N',N'-tetraacetic acid.
[2]Nitrilotriacetic acid.

Table 4 also indicates the iron (III) binding constant (K) of the chelators tested. The results demonstrate that only the chelators having an iron (III) binding constant of greater than $10^{22}$ have acceptable anti-microbial activity. Whilst the chelators of lower iron (III) affinity did have some anti-microbial activity in this test, the inhibition values obtained clearly indicate the inferiority of these materials.

Examples 4 to 7

Further Aerosol Compositions

DTPA salt compositions were prepared according to Table 5. 76 $mmol.kg^{-1}$ solutions of the indicated chelator-amine salts in 96:4 (w/w) ethanol/water, also containing perfume (1.5% w/w) and isopropyl myristate (0.33% w/w), were pressurised to about 2.7 bar with a proprietary mixture of propane, isobutane, and N-butane (CAP40, 22:24:54, ex Calor). The resulting pressurised systems, contained liquified propellant:base in the weight ratio 35:65, DTPA being present at about 13 $mmol.kg^{-1}$, based on the total weight of all components present, including the propellants. All of these products were homogeneous solutions.

TABLE 5

DPTA salts in 96% Ethanol and CAP40

| | Example | | | |
|---|---|---|---|---|
| Component | 4 | 5 | 6 | 7 |
| DTPA (as free acid) | 0.5 | 0.5 | 0.5 | 0.5 |
| Diisopropanolamine | 0.42 | 0 | 0 | 0 |
| AMP | 0 | 0.37 | 0 | 0 |
| 2-amino-2-butanol | 0 | 0 | 0.31 | 0 |
| Cyclohexylamine | 0 | 0 | 0 | 0.42 |
| Isopropyl myristate | 0.33 | 0.33 | 0.33 | 0.33 |
| Water | 2.55 | 2.56 | 2.55 | 2.55 |
| CAP40 | 35 | 35 | 35 | 35 |
| Ethanol | To 100 | To 100 | To 100 | To 100 |

All components are expressed as weight percent of the total components added.

Roll-On Compositions

Examples 8 to 11, illustrated in Table 6, were prepared in the following manner. The indicated chelator acid (1 g or 0.5 g) was added to 20 g of water. The pH was adjusted to about 7.0 by dropwise addition of 1M sodium hydroxide solution. Separately, hydroxypropylcellulose (HPC) (0.65 g) was added to ethanol (60 g), whilst shearing at a speed of about 8000 rpm on a Silverson L4RT mixer (ex. Silverson, Chesham, Bucks.). The resulting homogenous solution was allowed to cool to ambient temperature and fragrance oil and fragrance solubiliser were then added with stirring. The ethanolic HPC solution was then mixed with the aqueous solution of the chelator salt and the total weight adjusted to 100 g with water.

TABLE 6

60% Ethanol Roll-On Compositions

| | Examples | | | |
|---|---|---|---|---|
| Component | 8 | 9 | 10 | 11 |
| Na₃DTPA | 0.5 | 1.0 | 0 | 0 |
| Na₃EDTA | 0 | 0 | 0.5 | 1.0 |
| Ethanol | 60 | 60 | 60 | 60 |
| HPC | 0.65 | 0.65 | 0.65 | 0.65 |
| Cremophor RH410[1] | 0.2 | 0.2 | 0.2 | 0.2 |
| Fragrance | 1.5 | 1.5 | 1.5 | 1.5 |
| Water | to 100 | to 100 | to 100 | to 100 |

[1]Fragrance solubiliser (PEG-40 hydrogenated castor oil, ex BASF).

The amount of chelator indicated is the amount of free acid added—this was then adjusted to pH 7.0 with NaOH.

All components are expressed as weight percent of the total composition.

Examples 12 to 15, see Table 7, were prepared in an analogous manner to Examples 8 to 11; the only differences were the use of ethanolamine (EA) to bring the aqueous chelator solution to pH 7.0, the omission of the perfume solubiliser, and the incorporation of 70% ethanol in the final composition.

TABLE 7

70% Ethanol Roll-On Compositions

| | Examples | | | |
|---|---|---|---|---|
| Component | 12 | 13 | 14 | 15 |
| EA₃DTPA | 0.5 | 1.0 | 0 | 0 |
| EA₃EDTA | 0 | 0 | 0.5 | 1.0 |
| Ethanol | 70 | 70 | 70 | 70 |
| HPC | 0.65 | 0.65 | 0.65 | 0.65 |
| Fragrance | 1.5 | 1.5 | 1.5 | 1.5 |
| Water | to 100 | to 100 | to 100 | to 100 |

The amount of chelator indicated is the amount of free acid added—this was then adjusted to pH 7.0 with EA.

All components are expressed as weight percent of the total composition.

Examples 16 to 19, see Table 8, were prepared in an analogous manner to Examples 12 to 15; the only differences were the use of AMP to bring the aqueous chelator solution to pH 7.0 and the incorporation of 80% ethanol.

TABLE 8

80% Ethanol Roll-on Compositions

| | Examples | | | |
|---|---|---|---|---|
| Component | 16 | 17 | 18 | 19 |
| AMP₃DTPA | 0.5 | 1.0 | 0 | 0 |
| AMP₃EDTA | 0 | 0 | 0.5 | 1.0 |
| Ethanol | 80 | 80 | 80 | 80 |
| HPC | 0.65 | 0.65 | 0.65 | 0.65 |
| Fragrance | 1.5 | 1.5 | 1.5 | 1.5 |
| Water | to 100 | to 100 | to 100 | to 100 |

The amount of chelator indicated is the amount of free acid added—this was then adjusted to pH 7.0 with 2-amino-2-methyl-1-propanol (AMP).

All components are expressed as weight percent of the total composition.

Squeeze/Pump Spray Compositions

Examples 20 to 25, as illustrated in Table 9, were prepared in a similar manner to Examples 12 to 15. Chelator salts were formed by neutralising the chelator acid to pH 7.0 with the indicated base (1M sodium hydroxide solution or neat ethanolamine [EA]).

TABLE 9

70% Ethanol Squeeze/Pump Spray Compositions

| | Example | | | | | |
|---|---|---|---|---|---|---|
| Component | 20 | 21 | 22 | 23 | 24 | 25 |
| EDTA | 1.0 | 0 | 0 | 1.0 | 0 | 0 |
| DTPA | 0 | 1.0 | 0 | 0 | 1.0 | 0 |
| EDDHA[1] | 0 | 0 | 1.0 | 0 | 0 | 1.0 |
| 1 M NaOH base | yes | yes | yes | no | no | no |
| EA base | no | no | no | yes | yes | yes |
| Glycerol | 1.0 | 1.0 | 1.0 | 1.0 | 1.0 | 1.0 |
| Fragrance | 1.5 | 1.5 | 1.5 | 1.5 | 1.5 | 1.5 |
| Ethanol | 70 | 70 | 70 | 70 | 70 | 70 |
| Water | to 100 | to 100 | to 100 | to 100 | to 100 | to 100 |

[1]N,N'-ethylenebis [2-(2-hydroxyphenyl) glycine]

The amount of base used was that required to neutralise the chelator to pH 7.0 in 20 g of water. All other components are expressed as weight percent of the total composition. (The amount of chelator indicated is the amount of free acid added.)

Analogous squeeze/pump spray compositions were prepared with an 80% level of ethanol and AMP salts of the above chelators at levels of 0.5% and 1.0% by weight (of the chelator in the acid form). Further analogous squeeze/pump spray compositions were prepared also comprising 0.05% by weight of triclosan (2',4,4'-trichloro-2'-hydroxydiphenyl ether).

Further Aerosol Compositions

For each of Examples 26 to 32 (Table 10), DTPA (2.00 g) was added as a powder to demineralised water (2.40 g). To each mixture, the indicated organic amine(s) was added, drop-wise with stirring. The weight in grams of organic amine(s) added was four times the weight percentage indicated in Table 5. The resulting mixtures were each made up to 20 g with anhydrous ethanol and stirred until a homogeneous solution was obtained.

Independently, for each Example, a solution of anhydrous ethanol (30 g), isopropyl myristate (1 g) and butylated hydroxytoluene (0.1 g) was prepared. For each Example, this solution was mixed with 5 g of the appropriate amine-containing solution. To each mixture was then added fragrance (1.5 g) and anhydrous ethanol (up to 45 g). The resulting 45 g base compositions were made into aerosol products by the addition of 55 g of CAP40, using the same technique as described for Example 1.

TABLE 10

High Propellant Aerosol Compositions

| Component | \multicolumn{7}{c}{Example} |
|---|---|---|---|---|---|---|---|
|  | 26 | 27 | 28 | 29 | 30 | 31 | 32 |
| DTPA | 0.5 | 0.5 | 0.5 | 0.5 | 0.5 | 0.5 | 0.5 |
| BHT | 0.1 | 0.1 | 0.1 | 0.1 | 0.1 | 0.1 | 0.1 |
| Fragrance | 1.5 | 1.5 | 1.5 | 1.5 | 1.5 | 1.5 | 1.5 |
| AMP | 0 | 0.25 | 0 | 0 | 0.09 | 0 | 0 |
| DMAMP[1] | 0.49 | 0 | 0 | 0 | 0 | 0 | 0 |
| CHA[2] | 0 | 0.20 | 0.42 | 0 | 0 | 0 | 0 |
| DIPA[3] | 0 | 0 | 0 | 0.41 | 0.32 | 0 | 0 |
| t-BA[4] | 0 | 0 | 0 | 0 | 0 | 0.31 | 0 |
| DEHA[5] | 0 | 0 | 0 | 0 | 0 | 0 | 0.54 |
| IPM[6] | 1.00 | 1.00 | 1.00 | 1.00 | 1.00 | 1.00 | 1.00 |
| Water | 0.6 | 0.6 | 0.6 | 0.6 | 0.6 | 0.6 | 0.6 |
| CAP40 | 55 | 55 | 55 | 55 | 55 | 55 | 55 |
| Ethanol | to 100 | to 100 | to 100 | to 100 | to 100 | to 100 | to 100 |

All components are expressed as weight percent of the total components added.
[1]2-(N,N-dimethylamino)-2-methyl-1-propanol.
[2]Cyclohexylamine.
[3]Diisopropylamine.
[4]Tert-butylamine.
[5]N,N-diethylhexylamine.
[6]Isopropyl myristate.

All the above compositions were homogeneous solutions. A similar composition prepared using solely 0.37 g of AMP as the organic amine was cloudy and ultimately separated into two phases. These results illustrate the preference for non-hydroxylated or tertiary amines (ie. amines free of any O—H or N—H bonds) in such hydrophobic systems.

Examples 33 to 36 (Table 11) were prepared in an analogous way to Examples 26 to 32. Please note that these compositions each comprise 45% of hydrocarbon propellant.

TABLE 11

Further High Propellant Aerosol Compositions

| Component | \multicolumn{4}{c}{Example} |
|---|---|---|---|---|
|  | 33 | 34 | 35 | 36 |
| DTPA (as free acid) | 0.5 | 0.5 | 0.5 | 0.5 |
| BHT | 0 | 0.1 | 0.1 | 0.1 |
| Fragrance | 1.5 | 1.5 | 1.5 | 1.5 |
| AMP | 0.38 | 0.38 | 0.38 | 0.38 |
| Miglyol 840[1] | 5.0 | 0 | 0 | 0 |
| 1,2-pentanediol | 0 | 6.0 | 0 | 0 |
| 1,2-hexanediol | 0 | 0 | 3.0 | 0 |
| Propylene carbonate | 0 | 0 | 0 | 5.0 |
| Water | 1.9 | 1.9 | 2.0 | 0.3 |
| Ethanol | to 100 | to 100 | to 100 | to 100 |
| CAP40 | 45 | 45 | 45 | 45 |

All components are expressed as weight percent of the total components added.
[1]Propylene glycol dicaprate/caprylate, ex Condea.

Examples 33 to 36 were all homogeneous solution compositions. The ethanol and water in Examples 33 to 35 were added in the form of 96% w/w ethanol, whilst the ethanol and water in Example 36 were added in the form of 99.4% w/w ethanol. When analogous compositions were prepared without the glycol or derivative thereof, the resulting compositions were cloudy and ultimately separated into two phases. These results illustrates the preference for a glycol or derivative thereof when over 40% of hydrocarbon propellant is present. In addition, Example 36 illustrates a homogeneous solution aerosol composition comprising an ethanol carrier fluid, DTPA, AMP, and propylene carbonate, having an ethanol:water weight ratio of greater than 99:1.

Examples 37 to 40 (Table 12) were prepared in an analogous way to Examples 26 to 32. Please note that these compositions each comprise 55% of hydrocarbon propellant.

TABLE 12

Further High Propellant Aerosol Compositions

| Component | \multicolumn{4}{c}{Example} |
|---|---|---|---|---|
|  | 37 | 38 | 39 | 40 |
| DTPA (as free acid) | 0.5 | 0.5 | 0.5 | 0.5 |
| Fragrance | 1.5 | 1.5 | 1.5 | 1.5 |
| AMP | 0.38 | 0.38 | 0.38 | 0.38 |
| Miglyol 840[1] | 6.0 | 0 | 0 | 0 |
| 1,2-pentanediol | 0 | 6.0 | 0 | 0 |
| 1,2-hexanediol | 0 | 0 | 3.0 | 0 |
| 1,2-octanediol | 0 | 0 | 0 | 3.0 |
| Water | 0 | 0 | 0 | 1.6 |
| Ethanol | to 100 | to 100 | to 100 | to 100 |
| CAP40 | 55 | 55 | 55 | 55 |

All components are expressed as weight percent of the total components added.

Examples 37 to 40 were all homogeneous solution compositions. The ethanol and water in Example 40 was added in the form of 96% w/w ethanol, whilst in Examples 37 to 39, anhydrous ethanol was used. When analogous compositions were prepared without the glycol or derivative thereof, the resulting compositions separated into two phases. These results illustrate the preference for a glycol or derivative thereof when over 50% of hydrocarbon propellant is present. In addition, Examples 37 to 39 illustrate homogeneous solution aerosol compositions comprising an ethanol carrier fluid, DTPA, AMP, and a glycol or derivative thereof, having an ethanol:water weight ratio of greater than 99:1.

Tetraalkylammonium-DTPA Aerosol Compositions

The tetraalkylammonium-DTPA salt compositions indicated in Table 13 were prepared in a similar manner to Examples 26 to 32. The indicated tetraalkylammonium hydroxide salts were used, instead of the amines of Examples 26 to 32, to form the DTPA salts according to following equation:

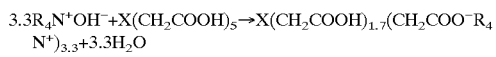

$3.3R_4N^+OH^- + X(CH_2COOH)_5 \rightarrow X(CH_2COOH)_{1.7}(CH_2COO^-R_4N^+)_{3.3} + 3.3H_2O$ where R is methyl, ethyl, or n-butyl and X is the DTPA backbone group which links the acetate groups.

TABLE 13

Tetrabutylammonium-DTPA Aerosol Composition

| Component | Example 41 | Example 42 | Example 43 |
|---|---|---|---|
| DTPA (as free acid) | 0.5 | 0.5 | 0.5 |
| $Me_4N^+$ $OH^-$ | 0.38 | 0 | 0 |
| $Et_4N^+$ $OH^-$ | 0 | 0.62 | 0 |
| $Bu_4N^+$ $OH^-$ | 0 | 0 | 1.09 |
| IPM | 1.0 | 1.0 | 1.0 |
| Water[1] | 1.15 | 1.15 | 1.63 |
| CAP40 | 55 | 55 | 55 |
| Fragrance | 1.5 | 1.5 | 1.5 |
| BHT | 0.1 | 0.1 | 0.1 |
| Ethanol | to 100 | to 100 | to 100 |

All components are expressed as weight percent of the total components added.
[1] the water level excludes that formed from the reaction between the DPTA and the tetraalkylammonium hydroxide.

Aerosol Compositions with Polar Propellants

Examples 44 to 46 (Table 14) were prepared in a similar manner to Examples 26 to 32, with tetrabutylammonium hydroxide being used instead of a free amine for Example 44.

TABLE 14

Aerosol Compositions with Polar Propellants

| | Example | | |
|---|---|---|---|
| Component | 44 | 45 | 46 |
| DTPA | 0.5 | 0.5 | 0.5 |
| $Bu_4N^+$ $OH^-$ | 1.09 | 0 | 0 |
| AMP | 0 | 0.38 | 0.38 |
| IPM | 1.0 | 0.25 | 0.25 |
| Water | 1.64 | 17.5 | 0.5 |
| 1,1-difluoroethane | 35 | 0 | 35 |
| Dimethyl ether | 0 | 45 | 0 |
| Ethanol | to 100 | to 100 | to 100 |

Deodorancy Test 3

The deodorancy protocol previously described was used to compare the performance of Example 27 (vide supra) with that of Comparative Example C, the composition of which is indicated in Table 15 (together with a reproduction of the composition of Example 27, for convenience). Comparative Example C was prepared in an analogous manner to Example 27.

TABLE 15

Example 27 vs. Control

| Component | Example C | Example 27 |
|---|---|---|
| DTPA (as free acid) | 0 | 0.5 |
| BHT | 0 | 0.1 |
| Fragrance | 1.5 | 1.5 |
| AMP | 0 | 0.25 |
| Cyclohexylamine | 0 | 0.20 |
| Isopropyl myristate | 1.0 | 1.0 |
| Water | 0.6 | 0.6 |
| CAP40 | 55 | 55 |
| Ethanol | to 100 | to 100 |

TABLE 15-continued

Example 27 vs. Control

| Component | | Example C | Example 27 |
|---|---|---|---|
| Mean malodour | 5 hour | 0.87 | 0.71 |
| intensity | 24 hour | 1.77 | 1.35 |

All components are expressed as weight percent of the total composition.

The malodour differences between the compositions were significant at the 99% level after 5 and after 24 hours. (Minimum differences required for significance at the 99% confidence levels were:
after 5 hours: 0.13;
after 24 hours: 0.14.)

These results illustrate the excellent deodorancy performance achievable using a deodorant composition comprising an ethanol carrier fluid, DTPA, organic amine, and an additional anti-microbial agent.

Fragrance Intensity Test

The compositions indicated in Table 16 were prepared in a manner analogous to Examples 26 to 32 (with the use of 96% v/v ethanol rather than anhydrous ethanol). The compositions were applied and assessed in a manner analogous to the previously described deodorancy protocol, the only difference being that fragrance intensity in the axillae was assessed, rather than axillary malodour.

TABLE 16

Fragrance Intensity Benefit

| Component | | Example D | Example 47 |
|---|---|---|---|
| DTPA (as free acid) | | 0 | 0.5 |
| AMP | | 0 | 0.38 |
| Isopropyl myristate | | 0.33 | 0.33 |
| Water | | 0.50 | 0.50 |
| CAP40 | | 35 | 35 |
| Fragrance | | 1.85 | 1.85 |
| BHT | | 0 | 0.1 |
| Ethanol (96% v/v) | | to 100 | to 100 |
| Mean fragrance | 5 hour | 1.93 | 2.07 |
| intensity | 24 hour | 0.24 | 0.37 |

All components are expressed as weight percent of the total components added.

The differences in fragrance intensities observed were significant at the 95% level after 5 hours and were significant at the 99% level after 24 hours. These results illustrate that the anti-microbial benefit of compositions of the invention may manifest itself as enhanced fragrance intensity.

What is claimed:

1. An anti-microbial composition comprising:
   (i) a $C_1$ to $C_4$ monohydric alcohol carrier fluid, present at a level of at least 50% by weight of the total composition, excluding any volatile propellant present;
   (ii) an iron (III) chelator selected from the group consisting of:
      (a) N,N'-ethylenebis[2-(2-hydroxyphenyl)glycine],
      (b) triethylenetetraaminehexaacetic acid, and
      (c) diethylenetriaminepentaacetic acid
   (iii) a solubility promoter selected from the group consisting of:
      (a) water;
      (b) an organic amine;
      (c) a polyhydric alcohol or derivative thereof;
      (d) a volatile propellant having fluorine-carbon or oxygen-carbon bonds;
      (e) any combination of (a) to (d).

2. An anti-microbial composition according to claim 1, that is a deodorant composition for use on the human body or on apparel worn in close proximity thereto.

3. An anti-microbial composition according to claim 1, that is a homogeneous solution.

4. An anti-microbial composition according to claim 3, that is a homogeneous solution in aqueous ethanol.

5. An anti-microbial composition according to claim 1, wherein the weight ratio of $C_1$–$C_4$ monohydric alcohol carrier fluid to water is greater than 65:35.

6. An anti-microbial composition according to claim 1, wherein the weight ratio of $C_1$–$C_4$ monohydric alcohol carrier fluid to water is greater than 75:25 and the solubility promoter comprises an organic amine.

7. An anti-microbial composition according to claim 6, wherein the organic amine is present at a level sufficient to neutralize at least 60% of any acid groups on the iron (III) chelator.

8. An anti-microbial composition according to claim 6, wherein the organic amine is present at a level sufficient to lead to an aqueous solution of the chelator salt having a pH of between 6 and 8 at a molar concentration of chelator salt equal to that present in the composition.

9. An anti-microbial composition according to claim 1, wherein the chelator is present at a concentration of 0.01% to 10% by weight of the composition, excluding any volatile propellant present.

10. An anti-microbial composition according to claim 1, comprising an additional anti-microbial agent.

11. An anti-microbial composition according to claim 10 wherein the additional anti-microbial agent is a cationic bactericide.

12. An anti-microbial composition according to claim 1, comprising fragrance material at up to 4% by weight of the composition, excluding any volatile propellant present.

13. An anti-microbial composition according to claim 1, that contains a volatile propellant.

14. An anti-microbial composition according to claim 13, wherein the volatile propellant comprises from 30 to 99% by weight of the total composition.

15. An anti-microbial composition according to claim 14, that contains greater than 40% by weight of volatile propellant and a solubility promoter selected from the group comprising:
 (a) an organic amine free of any N—H bonds and/or O—H bonds;
 (b) an organic amine and a polyhydric alcohol or derivative thereof;
 (c) an organic amine and a volatile propellant having fluorine-carbon or oxygen-carbon bonds.

16. An anti-microbial composition according to claim 13, wherein the weight ratio of $C_1$–$C_4$ monohydric alcohol carrier fluid to water is between 95:5 and 99:1.

17. An anti-microbial composition according to claim 13, wherein the weight ratio of $C_1$–$C_4$ monohydric alcohol carrier fluid to water is greater than 99:1.

18. An anti-microbial composition comprising:
 (i) a $C_1$ to $C_4$ monohydric alcohol carrier fluid, present at a level of greater than 50% by weight of the total composition, excluding any volatile propellant present
 (ii) an iron (III) chelator selected from the group consisting of:
  (a) N, N'-ethylenebis[2-(2-hydroxyphenyl)glycine],
  (b) triethylenetetraaminehexaacetic acid, and
  (c) diethylenetriaminepentaacetic acid and
 (iii) water as a solubility promoter.

* * * * *